United States Patent [19]
Kidwell

[11] Patent Number: 5,369,007
[45] Date of Patent: * Nov. 29, 1994

[54] MICROASSAY ON A CARD

[75] Inventor: David A. Kidwell, Alexandria, Va.

[73] Assignee: The United States of America as represented by the Secretary of the Navy, Washington, D.C.

[*] Notice: The portion of the term of this patent subsequent to Apr. 6, 2010 has been disclaimed.

[21] Appl. No.: 981,857

[22] Filed: Aug. 26, 1992

Related U.S. Application Data

[63] Continuation of Ser. No. 578,390, Sep. 7, 1990, Pat. No. 5,200,321.

[51] Int. Cl.$^5$ .................. G01N 33/53; G01N 33/543
[52] U.S. Cl. .................. 435/7.9; 435/7.92; 435/7.95; 435/805; 435/810; 435/969; 435/970; 436/518; 436/531; 436/169; 436/170; 42/56; 42/57; 42/58; 42/60
[58] Field of Search .................. 435/7.9, 7.92–7.95, 435/805, 810, 967, 969, 970; 436/518, 528, 531, 169, 170, 805, 808, 810; 422/56–58, 60

[56] References Cited

U.S. PATENT DOCUMENTS

| | | | |
|---|---|---|---|
| 4,128,692 | 12/1978 | Reid | 427/212 |
| 4,258,001 | 3/1981 | Pierce et al. | 422/56 |
| 4,299,916 | 11/1981 | Litman et al. | 435/6 |
| 4,318,408 | 3/1982 | Korpman | 604/368 |
| 4,381,320 | 4/1983 | Nguyen | 427/44 |
| 4,389,513 | 6/1983 | Miyazaki | 525/186 |
| 4,391,904 | 7/1983 | Litman et al. | 435/7 |
| 4,394,930 | 7/1983 | Korpman | 220/444 |
| 4,446,232 | 5/1984 | Liotta | 422/56 |
| 4,559,050 | 12/1985 | Iskra | 604/368 |
| 4,787,949 | 11/1988 | Cole et al. | 156/222 |
| 4,826,759 | 5/1989 | Guire et al. | 435/4 |
| 4,916,056 | 4/1990 | Brown, III et al. | 435/7.9 |
| 4,920,046 | 4/1990 | McFarland et al. | 435/7.9 |
| 5,002,986 | 3/1991 | Fujiura et al. | 524/47 |
| 5,030,229 | 7/1991 | Yang | 604/385.1 |
| 5,065,752 | 11/1991 | Sessions et al. | 128/156 |
| 5,087,506 | 2/1992 | Palumbo | 428/194 |
| 5,196,302 | 3/1993 | Kidwell | 435/4 |
| 5,200,321 | 4/1993 | Kidwell | 435/7.9 |

OTHER PUBLICATIONS

Curme, et al. "Multilayer Film Elements For clinical Analysis: General Concepts printed in Clin. Chem". 24/8, 1335–1341 (1978).
Zuk et al. "Enzyme Immunochromatography—A Quantitative Immunoassay Requiring No Instrumentation", printed in Clin. Chem 31/7, 1144–1150 (1985).
Ramp TM ProgestUrine TM brochure (1986), PDG:001-A 886.
"Enzyme", printed in Analytical Chemistry, vol. 56, No. 8, Jul. 1984; 920A–922A, 924A, 926A, 928A, 930A–931A.
Ramp TM Urine hcG Assay brochure (1986), RMP002 30 M 0186.
Granite Diagnostics, Inc. "Description of the E-Z Screen Test System" Brochure Oct. 7, 1985.
Grenner et al. "Multilayer Fluorescent Immunoassay Technique" reprinted in Clinical-Chemistry, 34, 1865–1868, (1989).
Kidwell "Superabsorbent Polymers-Media For the Enzymatic Detection of Ethyl Alcohol in Urine", printed in Analytical Biochemistry, 182, 257–261 (1989), (Nov. 2).

Primary Examiner—Toni R. Scheiner
Attorney, Agent, or Firm—Thomas E. McDonnell; Barry A. Edelberg

[57] ABSTRACT

A microassay card includes an upper layer containing wells for receiving a liquid sample. A second layer of the card, beneath the first layer, includes a supporting surface bound to a reactive species. A third layer includes a superabsorbent support impregnated with an indicator. Typically, the indicator is a substrate for an enzyme, such as a reduced dye precursor and a source of hydrogen peroxide necessary for the action of the enzyme upon the substrate to cause a spectral change in the absorbent layer. By selecting the structure of the first and second layers, the card can be formatted for a displacement assay or a competitive assay. The microassay card of the present invention is particularly useful for drug testing.

18 Claims, 4 Drawing Sheets

MICROASSAY ON A CARD

This application is a continuation of U.S. Ser. No. 07/578,390, filed Sep. 7, 1990, now U.S. Pat. No. 5,200,321.

BACKGROUND OF THE INVENTION

1. Field of the Invention

This invention relates to a rapid, field-portable assay for substances, particularly drugs of abuse, that provides a positive signal in the presence of the substance.

2. Description of the Prior Art

At present, the well-publicized problems associated various drugs of abuse and the National policies associated with the "war against drugs" have led to an increased need for simple, rapid relatively inexpensive, and accurate methods for detecting drugs of abuse in fluid samples. Currently available methods and kits for testing for various chemical and biological species such as drugs of abuse, hormones, etc. suffer from the fact that these often involve relatively expensive, bulky, non-portable instrumentation. Therefore, the tests must be performed in a controlled environment.

The current systems thus often require expensive high precision instruments to measure the color change which increases the overall cost of the analysis, and requires the expertise of lab personnel. Similarly, many tests, while having a simple color change indication, involve several solutions that must be applied to a test strip. These solutions also increase the cost of the test, may require special storage conditions, increase the possibility for mistakes and also involve specialized personnel. These tests are less likely to be mobile and thus cannot be carried along or employed easily or safely by individuals conducting the test, such as lab personnel or law enforcement officers. It is thus highly desirable to develop a simple and inexpensive system which is highly mobile, yet can provide a fast, reliably accurate indication of the presence of a suspected chemical.

One enzymatic assay system using a multi-layer dry film and marketed by Eastman Kodak Co. is described in Curme et al, Clin. Chem. 24/8, 1335-1342 (1978). That system includes an upper spreading or metering layer, a reagent layer containing a binder and all required reagents (buffer, enzymes, dye precursors) beneath the metering layer and a transparent support beneath the enzyme-containing layer. The Kodak system, however, does not perform immunoassays and lacks a membranous layer for controlling the velocity of sample travel within the enzyme-containing layer. The metering layer of the Kodak system reduces the possibility of overloading of the enzyme, but does not use a membrane to effectively control the velocity at which the sample moves once it reaches the enzyme-containing layer. Thus, the sensitivity of the Kodak assays may be decreased by incomplete enzymatic reaction. Also, this lack of appropriate velocity control prevents effective use of the Kodak system for immunoassays.

Greener et al, in "Multilayer Fluorescent Immunoassay Technique", Clinical Chemistry, Vol. 35, No. 9 (1989) discloses a multilayer fluorescent immunoassay. That immunoassay uses a multilayered structure including, from top to bottom, a spreader layer, a top coat layer for filtering out potentially interfering proteins, a signal layer of antibody-indicator-hapten conjugate in an agarose matrix, and a polyester film base. The observed fluorescence is inversely proportional to the concentration of assayed substance present in the sample. Also, since fluorescence must be measured, the immunoassay requires instrumentation.

SUMMARY OF THE INVENTION

Accordingly, it is an object of this invention to provide a highly mobile, fast, reliable and accurate indication for the presence of a suspected chemical which provides a positive signal in proportion to the concentration of the suspected chemical.

It is another object of this invention to provide an which does not require expensive or bulky equipment.

It is a further object of the present invention to provide assay which can be reliably and accurately performed by untrained personnel.

It is yet another object of the present invention to determine the presence of a suspected chemical in an assay through a convenient and simple enzyme-based immunoassay.

These and additional objects of the invention are accomplished by a multi-layer microassay card. An upper layer contains wells for receiving the sample and any necessary buffer system, in dry form. A second layer of the card, beneath the first layer, includes a supporting membrane bound (covalently or noncovalently) to a reactive species, for example, an antibody which is specific to a chemical to be assayed and which is bound with the chemical and an enzyme or, if said buffer-containing layer includes an antibody-enzyme conjugate which specifically binds to the biologically active chemical, the biologically active chemical itself. The second also layer includes a control membrane which controls the velocity of fluid travel therethrough. A third layer, beneath the second layer, includes a superabsorbent support impregnated with a substrate for the enzyme, and also includes any indicator, such as a reduced dye and a source of hydrogen peroxide (if the enzyme requires hydrogen peroxide as a cofactor), necessary for the action of the enzyme upon the substrate to cause a spectral change in the absorbent layer.

BRIEF DESCRIPTION OF THE DRAWINGS

A more complete appreciation of the invention will be readily obtained by reference to the following Detailed Description of the Invention and the accompanying drawings in which like numerals in different figures represent the same structures or elements, wherein.

DETAILED DESCRIPTION OF THE INVENTION

The assay utilizes antibody-antigen recognition of the chemical of interest, amplification of that recognition, and subsequent spectral indication of the chemical's presence. The key component of the assay is a specialized test card, hereinafter referred to as a microassay on a card or MAC. Preferably, the chemicals sought to be recognized are those of low molecular weight, that is, less than about 1000 AMU. Most preferably, the chemicals sought to be identified are those commonly known as drugs of abuse—cocaine, PCP, LSD, and morphine, for example.

Figure 1:
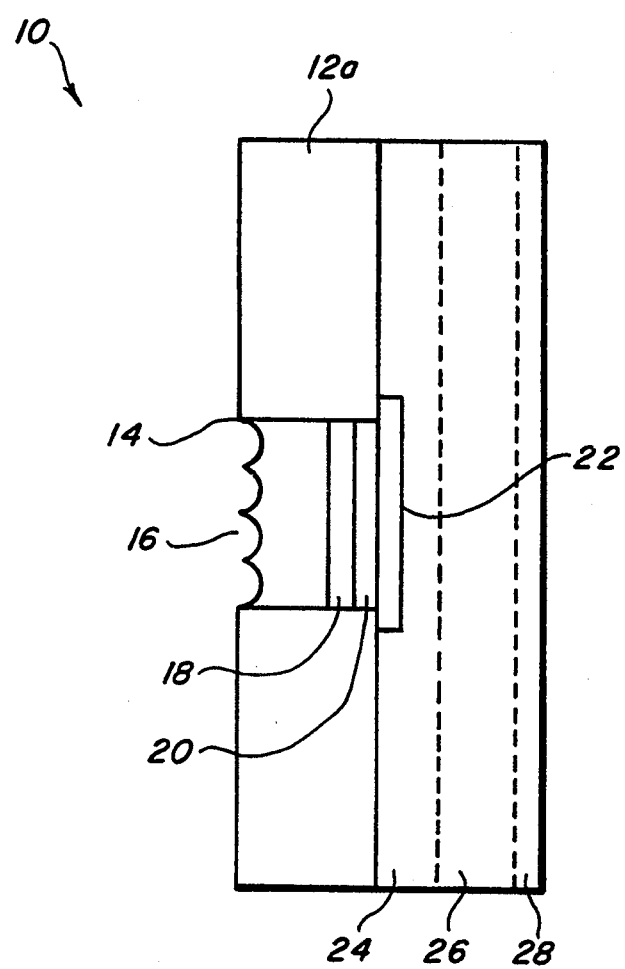
FIG. 1 is a schematic side view of a card according no the present invention.

As shown in FIG. 1, one preferred embodiment of the microassay card according to the present invention is a three section or layer slide 10. The first section 12 includes a hydrophobic layer 12a containing the wells 14. The test fluid 16 is placed in each well and is held by surface tension. Optionally, the first section also includes, as a sublayer, layer 18, in the well, composed of a porous material, such as filter paper, containing a pH buffer. The second section 20 also resides in the well and contains a monoclonal antibody chemically bound to the surface of a membrane. The antibody has preabsorbed a drug-enzyme conjugate. The second section 20 includes a semipermeable membrane 22 beneath well 14 to control the timing of the fluid flow. The timing is set such that the test fluid is drawn through the optional buffer layer 18 and monoclonal antibody-containing surface in the optimum time required for the desired sensitivity, usually approximately two minutes. Section three, 26, is a super-absorbent polymer impregnated with the substrate for the enzyme. The super-absorbent polymer permits larger liquid samples to be applied and increases sensitivity. Preferably, section three, 26, includes, as a sublayer, a contrasting backing layer 24 that surrounds the well 14 and semipermeable membrane 22 and provides a white or otherwise suitably contrasting background for the developed color spot. Section three can optionally include, as a sublayer, a protective layer, 28, for example tissue paper, that protects the superabsorbent polymer against abrasion and becomes transparent when wetted by the test fluid 16.

The microassay card can be formatted in one of two modes—a displacement mode or a competitive mode. The displacement mode is preferred for ease of manufacture of a test strip for the assay, while the competitive mode is preferred for assays requiring greater sensitivity.

The arrangement of the reactive species within the layered card will determine whether the card is formatted for a displacement assay or a competitive assay. Table I shows various possible arrangements. In Table I, layer A (section 1) is the optional buffer layer, layer B (also section 1) is the layer which first receives the sample added to the well (sample-receiving layer)- (However, if a buffer is employed, layers A and B may be combined, or the sample preferably passes through layer A before passing through layer B), layer C (section 2) is the reactive species bound to a surface (such as a membrane) and layer D (also section 2) is a control membrane for controlling the velocity of fluid travelling through a reactive species-bound layer. Where layer C is not present, the control membrane of layer D the is reactive species-bound membrane. A "—" indicates either that the layer is absent or does not contain any reactive species.

TABLE I

| Type of Assay | Arrangement of Reactive Species | | | |
| --- | --- | --- | --- | --- |
| | Layer A | Layer B | Layer C | Layer D |
| Displacement | | | | |
| 1. | optional | — | antibody-enzyme conjugate + immobilized substance | membrane |
| 2. | optional | — | — | antibody-enzyme conjugate + substance bound to membrane |
| 3. | optional | — | substance-enzyme conjugate + immobilized antibody | membrane |
| 4. | optional | — | — | substance-enzyme conjugate + antibody bound to membrane |
| Competitive | | | | |
| 5. | optional | antibody-enzyme conjugate | substance bound to surface | membrane |
| 6. | optional | substance-enzyme conjugate | antibody bound to surface | membrane |
| 7. | optional | antibody-enzyme conjugate | — | substance bound to membrane |
| 8. | optional | substance-enzyme conjugate | — | antibody bound to membrane |

Figure 2:
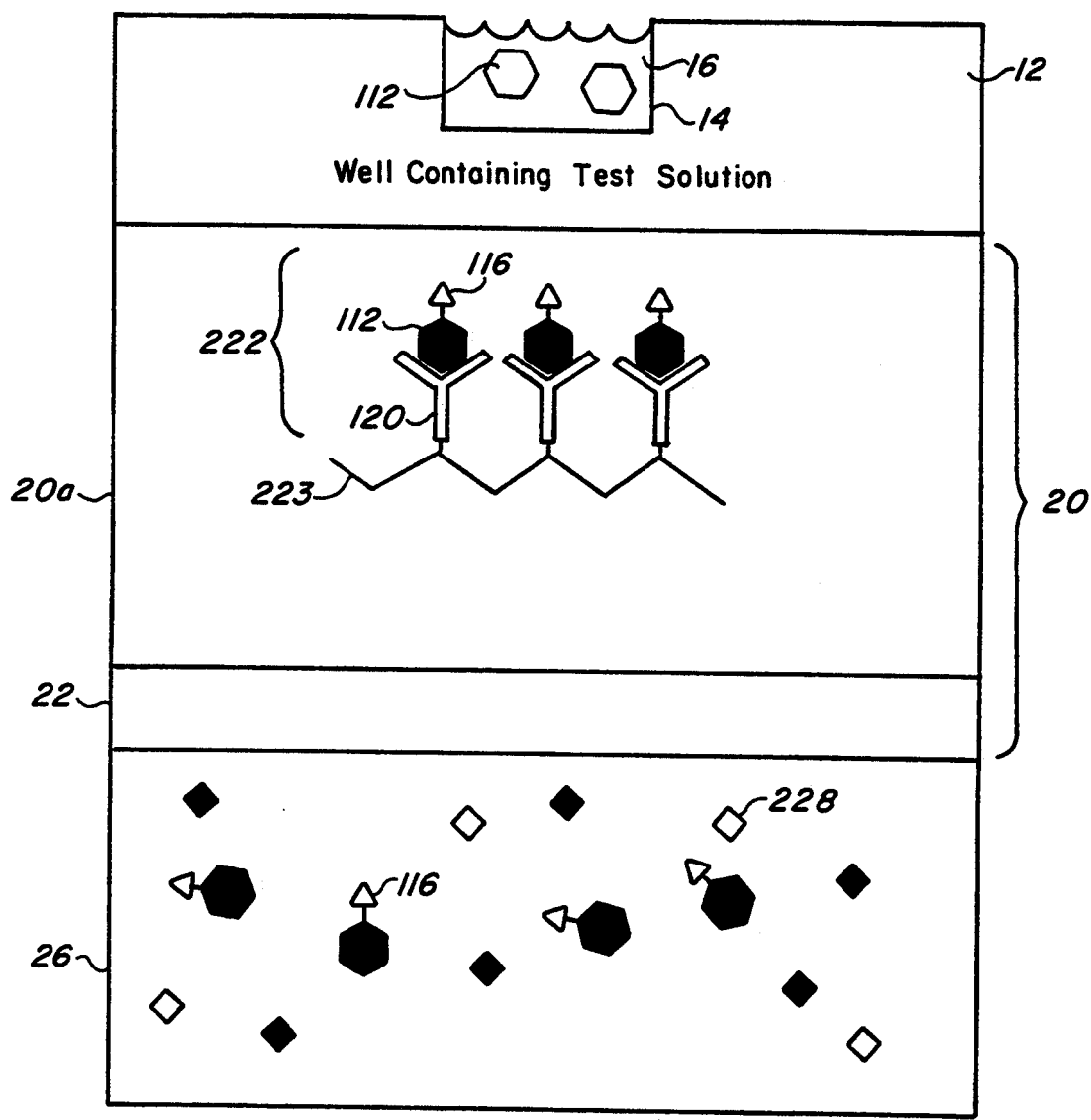
FIG. 2 shows the components of a test card designed for displacement-type assays, as shown in Table I, scheme 3.
Figure 3:
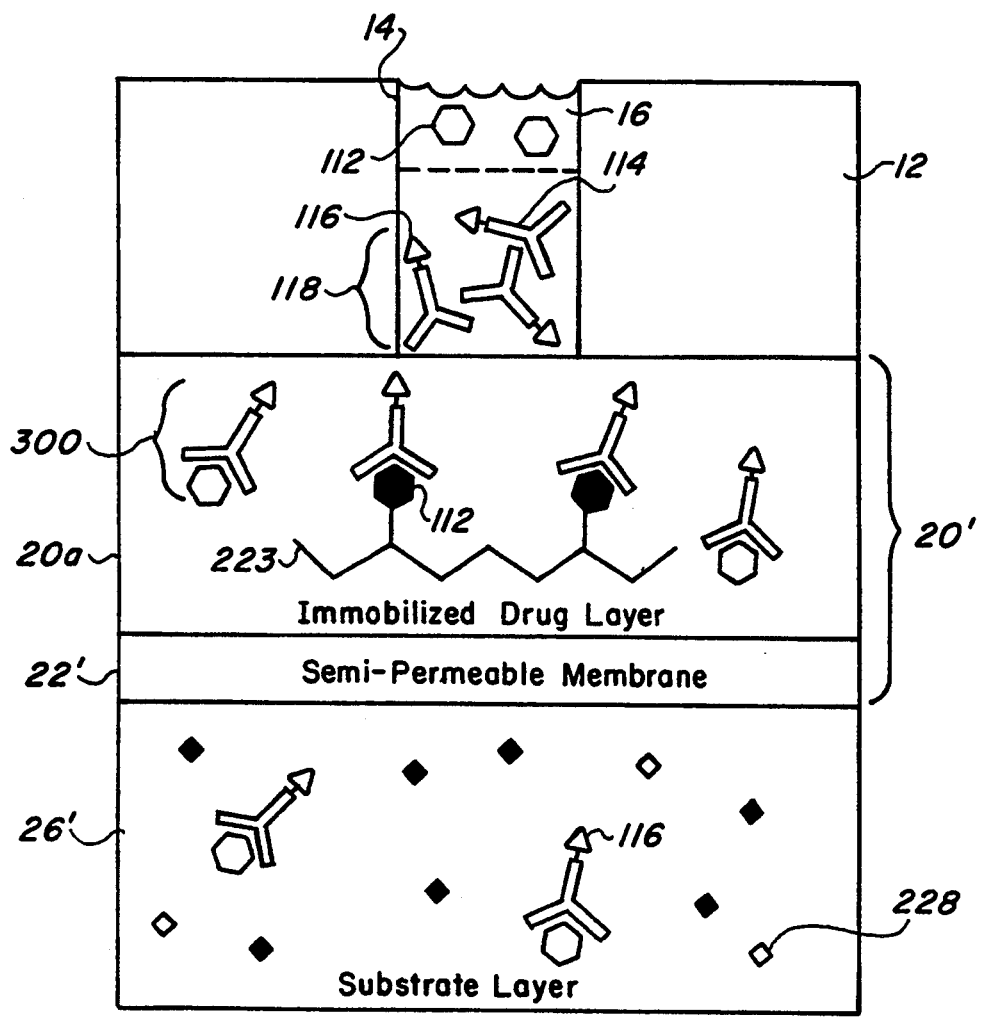
FIG. 3 shows the components of a test card designed for competitive-type assays, as shown in Table I, scheme 5.

FIG. 2 shows one embodiment of a MAC designed for displacement mode and FIG. 3 shows one embodiment of a MAC designed for the competitive mode. In the first layer 12 (section 1), well 14 contains the fluid sample 16 which may or may not contain the suspected substance 112. In the embodiment of (FIG. 3), this well also contains an antibody 114—enzyme 116 conjugate 118. In FIG. 2, layer 20 (section 2) comprises antibody 120, with presorbed (shaded) suspected substance 112—enzyme 116 conjugate, 222, immobilized on filter paper or other suitable supporting membrane 223. In FIG. 3, the suspected substance 112 is immobilized (immobilized suspected substance 112 is shaded) on the filter paper or otherwise suitable supporting membrane 223 of layer 20'. Layer 20, 20' also comprises some means, such as semipermeable membrane 22, 22' for regulating the flow of sample through the layer. Layer 26 (FIG. 2), 26' (FIG. 3) is a superabsorbent layer impregnated with the substrate 228 for the enzyme 116.

Both the substance-enzyme conjugate and the antibody-enzyme conjugate are specific for the substance being assayed. The substance in the substance-enzyme conjugate is the same as the substance assayed. Similarly, the antibody in the antibody-enzyme conjugate must be specific for the substance assayed. The enzyme must be one that catalyzes the substrate reaction quickly (minutes), produces a detectable spectral change and is sensitive in an enzyme detection system. Preferably, enzymes used in oxidative or hydrolysis systems (such as alkaline phosphatase with a hydrolysis indicator, for example: bromocresolsulfophthalein monophosphate) are used, since these tend to be faster and more sensitive than reductive systems. Most preferably, horseradish peroxidase or alkaline phosphatase is used.

The first basic section, the well containing the test solution, has several purposes in both the competitive mode and the displacement mode. The first basic section serves to hold the fluid sample containing the suspected substance in place and guide it through the other sections. An optional purpose of the first basic section is to properly buffer the sample. In the competitive mode, this first basic section must also contain an antibody-enzyme or substance-enzyme conjugate so that the fluid sample will carry the antibody-enzyme or substance-enzyme conjugate, respectively, into the other sections.

Preferably, the first basic section holds the sample in place by surface tension and contains a pH buffer and, if the MAC is in the competitive mode, the specific antibody-enzyme or substance-enzyme conjugate. Most preferably, as shown in FIG. 1, the first basic section 12 comprises two separate layers, the first being a hydrophobic layer 12a containing sample wells 14 and the second being layer 18, containing a pH buffer and, if in the competitive mode, an antibody-enzyme or substance-enzyme conjugate that will be dissolved by the sample. Layer 18 is made of filter paper or an otherwise absorbent substrate.

The second basic section 20, in the displacement MAC of FIG. 2, comprises immobilized antibodies preloaded with substance-enzyme conjugates. This section is where a displacement reaction will take place if the suspected substance is present in the sample. If the fluid sample contains the suspected substance, the substance will displace the substance-enzyme conjugate from the antibodies. Therefore, the more suspect substance that is present, the more substance-enzyme conjugate that will be freed, to pass on to the next section to be identified. The section also has two other purposes. First, to regulate the flow of the sample through the section, so that the sample has time to react, and second, to filter out any impurities such as blood cells that may interfere with or color later reactions.

In the MAC of FIG. 3, which is in the competitive mode, the second basic section 20' comprises immobilized suspected substance 112. If the fluid sample contains the suspect substance 112, then the substance 112 will bind with the antibody-enzyme conjugate 118 in the first section. No free antibodies will be available to bind to the immobilized substance 112 in section 20', and substance-antibody-enzyme conjugate 300 will pass on into layer 26' to be identified. The more suspected substance that is present in the sample, the more antibody sites it will bind to and, hence, the more substance-antibody-enzyme conjugate will be freed to pass into layer 26'.

The requirements for the antibodies used are that the antibodies be capable of specifically binding the suspected substance. The preferred affinity of the antibodies will depend on the type of assay. In a displacement mode, the preferred affinity is between about $10^6$ and about $10^8$, with an affinity of about $10^6$ being most preferred. In a competitive mode, the preferred affinity is between about $10^8$ and about $10^{11}$, with an affinity of about $10^{10}$ being most preferred. Since antibodies to low molecular weight chemicals, particularly drugs of abuse, are often expensive and of low quality, it is most preferred to employ monoclonal rather than polyclonal antibodies.

The second basic section 20, 20' is the site of the competition/displacement reaction and also serves to regulate the flow of the sample. Generally, the second basic section 20, 20' comprises two sublayers. The first sublayer is layer 20a (FIG. 2), 20a' (FIG. 3) having the immobilized reactive species and the second layer 22 (FIG. 2), 22' (FIG. 3) is a semipermeable membrane, capable of regulating the fluid flow. The reactive species (antibody/suspect chemical, suspected substance/enzyme, antibody or suspect substance) is preferably immobilized on supporting membrane 223. The immobilization may be by covalent or non-covalent binding of to a non-crystalline membrane, such that there is a free flow of the fluid through the membrane. Examples of such membranes are cellulose, nitrocellose, and mixed acetate cellose-nitrocellose, polycarbonate and polysulfone. Preferably, the reactive species is immobilized by drawing a solution of the reactive species through the membrane and letting the membrane dry. Most preferably, a vacuum applicator is used. The semipermeable membrane can be any membrane that, together with the supporting membrane, regulates the fluid flow rate so that the proper reactions take place. Preferably, this interaction time is between about one to about five minutes, with two minutes being most preferred. Hence, one can vary the pore size and the area of the supporting and semipermeable membranes to achieve the proper interaction time. The smaller the pore size and the smaller the surface area of the membranes, the longer the interaction time and the greater the sensitivity. Also, depending upon the pore size of the supporting membrane, an additional semipermeable membrane may not be required. In the displacement mode using a nitrocellose membrane, optimum performance in both time and sensitivity results from 0.45 $\mu m$ pore size, with a three-sixteenth inch diameter membrane and application of 40 $\mu l$ test solution to obtain a two minute draw-though time. For a 3/16 inch hole size, using polycarbonate and polysulfone membranes, the approximate draw-through times are shown on Table II and Table III.

TABLE II

| Polycarbonate | |
|---|---|
| Pore Size ($\mu m$) | Time (secs) |
| 0.015 | ∞ (does not draw through) |
| 0.1 | 800 |
| 0.2 | 135 |
| 0.4 | 68 |

TABLE III

| Polysulfone | |
|---|---|
| Pore Size ($\mu m$) | Time (sec) |
| 0.1 | 78 |
| 0.2 | 65 |

The third basic section 26 (FIG. 2), 26' (FIG. 3), a superabsorbent layer impregnated with substrates for the enzyme 116, serves to produce a detectable spectral change (from the reaction of the enzyme on the substrate) proportional to the amount of enzyme and, therefore, proportional to the concentration of suspect substance 112 in the fluid sample. Because the signal from the indicator is directly, rather than inversely, proportional to the concentration of the suspected substance, there is no need for a spreading layer in the present invention and the results are easy to interpret. Preferably, the third basic section 26, 26' comprises two sublayers, a superabsorbent polymer layer impregnated with a substrate for the enzyme 116 and a layer of contrasting backing, such as blotter paper 24, to provide a white or otherwise contrasting background for better identification of any spectral change. Most preferably, the third section 26, 26' also includes a protective layer 28 (made of tissue paper for example) that is or becomes transparent when wet, in order to protect the superabsorbent polymer from abrasion during handling.

Superabsorbent polymers are a recognized class of materials. Often, the are formed of either salts of polyacrylic acid or grafted acrylic acid on a starch backbone. Superabsorbent polymers can absorb up to 2000 their weight in water (preferably an absorptive capacity of at least about 200 mL distilled water/100 cm$^2$). When hydrated, the superabsorbent polymer forms an essentially transparent (usually colorless and clear) gel.

A number of superabsorbent polymeric materials are known and are suitable for use in the present invention. In the preferred embodiments, the superabsorbent polymers used will be capable of absorbing at least about 500 times their own weight in water.

The superabsorbent polymer not only permits testing of larger liquid samples, it also allows increased sensitivity. Preferably, the polymer should absorb quickly, yielding a small spot, uniform in appearance. For example, Grain Products Corporation L413 paper (1 g/cm$^2$, superabsorbent polymer with an absorptive capacity of 225 mL distilled water/100 cm$^2$) a three layer paper including blotter paper, superabsorbent polymer and tissue paper, may be used. Another suitable paper is Grain Products Corporation L415 paper, which has a similar construction to that of the L413 paper (1.3 g/cm$^2$ superabsorbent polymer with an absorptive capacity of 425 mL distilled water/cm$^2$). These commercially available papers are exemplary only. No limitation to these specified commercial materials is in any way intended.

A number of other suitable superabsorbent materials which are widely known and readily available can be employed in the present invention. Such materials, which will absorb many times their own weight of fluid, include one type wherein particles or fibers may be described chemically as having a backbone of natural or synthetic polymers with hydrophilic groups or polymers containing hydrophilic groups being chemically bonded to the backbone or in intimate admixtures therewith. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to improve their water-insolubility. These same polysaccharides may also serve, for example, as the backbone onto which other polymer moieties may be bonded by graft copolymerization techniques. Such grafted polysaccharides and their method of manufacture are described in U.S. Pat. No. 4,105,033 (Chatterjee et al), incorporated herein by reference. These polysaccharide chains have grafted thereon a hydrophilic chain such as hydrolyzed polyacrylonitrile chains and copolymers of polyacrylamide and polysodium acrylate.

In addition to modified natural and regenerated polymers, the superabsorbent polymers may include hydrocolloid particle components comprising wholly synthetic hydrophilic particles. Examples of these components are polyacrylonitrile fibers which may be modified by grafting moieties thereon such as polyvinyl alcohol chains, polyvinyl alcohol itself, hydrophilic polyurethane, poly(alkylphosphonates), partially hydrolyzed polyacrylamides (e.g., poly(N-N-dimethyl acrylamide), sulphonated polystyrene, or a class of poly(alkylene oxide), such as described in U.S. Pat. No. 4,559,050 (Iskra), incorporated herein by reference. These highly hydrophilic synthetic polymers may be modified by other chemical treatments such as cross-linking or hydrolysis. Other suitable compounds include the nonionic hydrophilic polymers such as polyoxyethylene, polyoxypropylene and mixtures thereof which have been suitably cross-linked, either chemically or by irradiation. Still another more recent type of superabsorbent component suitable for use in the present invention is a derivative of isobutylene-maleic anhydride copolymer. Further discussion of appropriate superabsorbent materials may be found in my copending U.S. patent application Ser. No. 07/574,175 entitled "Enzymatic Assays Using Super Absorbent Materials", filed Aug. 29, 1990, now U.S. Pat. No. 5,196,302, the entirety of which is incorporated by reference herein.

As for the substrate, any substrate that will work with the enzyme to produce a spectral change may be used, as long as both substrate and enzyme are fairly stable when dry and capable of reacting when wetted. The spectral change can be fluorescent, chemiluminescent or visual. The detectable change may be in absorption or emission. A visual color change is desirable for use without instrumentation. Also, the intensity of any spectral change is preferably proportional to the concentration of the substance being assayed. Preferably, reduced dye precursors are used as the substrate. The reaction is:

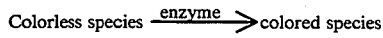

Colorless species $\xrightarrow{\text{enzyme}}$ colored species

This reaction is catalyzed by a number of enzymes, one of which is preferred—horseradish peroxidase. Since a source of hydrogen peroxide is needed that will remain stable and not destroy the detection reagents (as liquid hydrogen peroxide, which also evaporates, would) a solid form of hydrogen peroxide must be incorporated into the substrate (the reduced dye precursor). Preferably, sodium peroxide or sodium perborate are used, with sodium perborate being most preferred.

The reduced dye precursors used in the color generating system are air stable, sensitive, and produce an air stable intense color. Typical reduced dye precursors ar 4-Chloro-1-naphthol; o-phenylenediamine; 3-amino-9-ethyl carbazole; 2,2'-Azino-di(3-ethylbenzthiazolone); Hanker-Yates reagent; 3-methyl-2-benzothiazolinone hydrazone hydrochloride (MBTH)+3-Dimethylaminobenzene carboxylic acid (DMAB); 4-Aminoantipyrene+a phenol; 3,3'-Diaminobenzidine and its derivatives, such as 3,3',5,5'-Tetramethylbenzidine, o-dianisidine, and Dicarboxidine. Preferably, the dye precursor is a combination of 4-chloro-1-naphthol and N,N-diethylphenylenediamine; N,N-dimethylphenylenediamine; or MBTH and DMAB. Most preferably, 4-chloro-1-naphthol or 3-methyl-2-benzothiazolinone+N,N-dimethylaminobenzoic acid are used. For increased stability of these dye precursors and the enzymes used, it is preferred to store the MAC in a sealed, airtight container.

The MAC, as described above, can be designed to assay for any substance suitable for immunoassay (i.e., any substance which can elicit antibody production, either by itself or in conjunction with a carrier protein) and specifically binds the antibody in aqueous media. For example, a MAC according to the present invention can be used to assay for progesterone (pregnancy testing), specific protein (toxins or any other protein whose presence is indicative of pathology such as part of the AIDS virus protein coat), or polysaccharides (bacterial cell wall elements).

Figure 4:
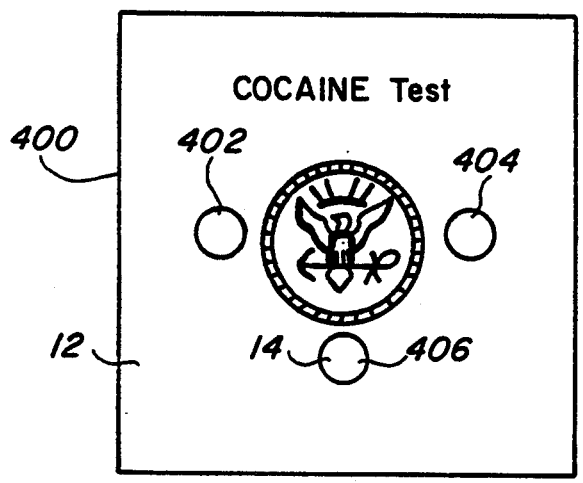
FIG. 4 is a top view of a preferred embodiment of a test card.
Figure 5:
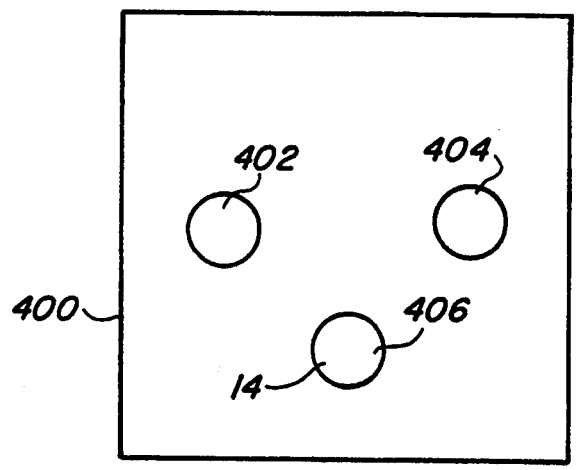
FIG. 5 is a bottom view of a preferred embodiment of a test card.

Since the first section may be designed to hold a single sample, a card 400 can be designed as shown in FIGS. 4 and 5, wherein several wells 14 are made in the first basic section, each well to hold a sample and test for an independent substance. In the embodiment of FIGS. 4 and 5, the card 400 is designed to assay for cocaine, the indicator turning blue if cocaine is present in the sample. Of course, card 400 could be designed to test for other substances and other indicators could be used. Preferably, one well 14 is for a negative control 402 (must remain colorless, i.e., cannot change spectral properties), one well 14 is for a positive control 404 (must turn blue, i.e., must change spectral properties) and one well 14 for the unknown sample 406. The color of the wells is read from the back of the card (FIG. 5).

The use of a card according to the present invention is quite simple, since no reagents need to be added to the test sample and all timing is controlled by the design of the MAC. An assay is performed by mixing a small amount of the suspect sample with some buffer solution and placing a drop of the test solution in each of the wells of a MAC card designed to indicate the presence of the suspected substance.

Having described the invention, the following examples are given to illustrate specific applications of the invention. These specific examples are not intended to limit the scope of the invention described in this application.

EXAMPLE

Antibodies to cocaine and PCP were made using rabbit serum. The cocaine antibodies were purified by affinity column chromatography and were of sufficient quality for use in the MAC assay. The preparation of the cocaine conjugate for injection into the rabbits is outlined below:

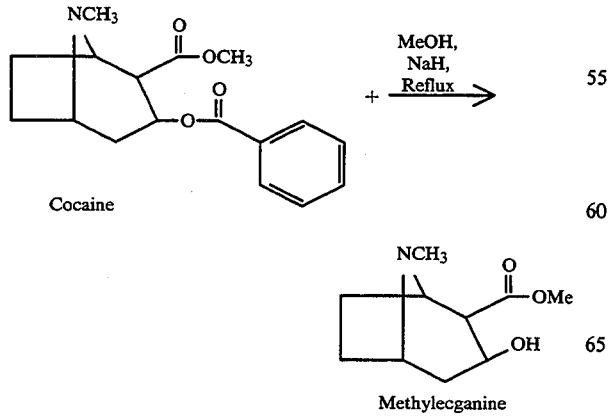

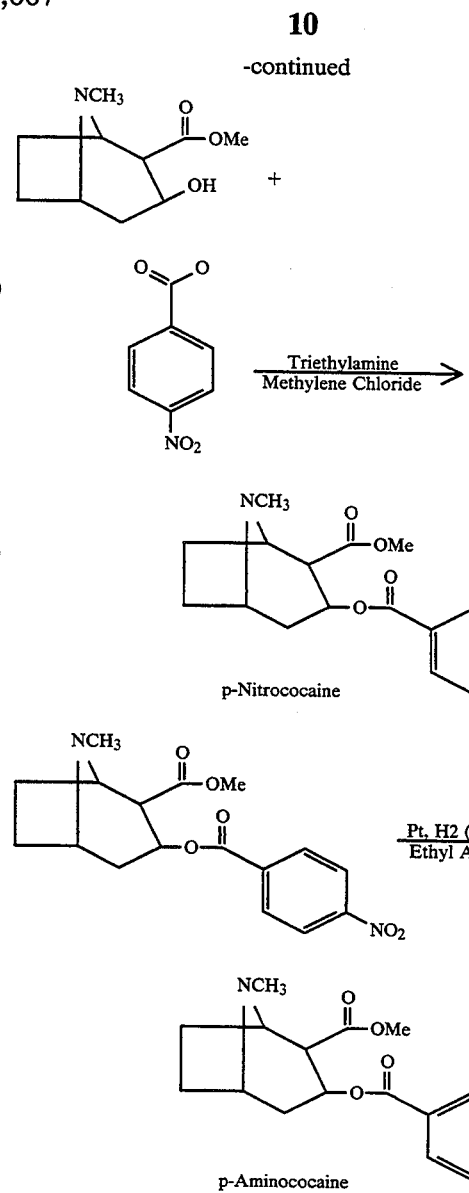

The derivatized cocaine molecule was attached to bovine antiserum albumin (BSA) as a carrier protein though a diazo linkage, as shown below:

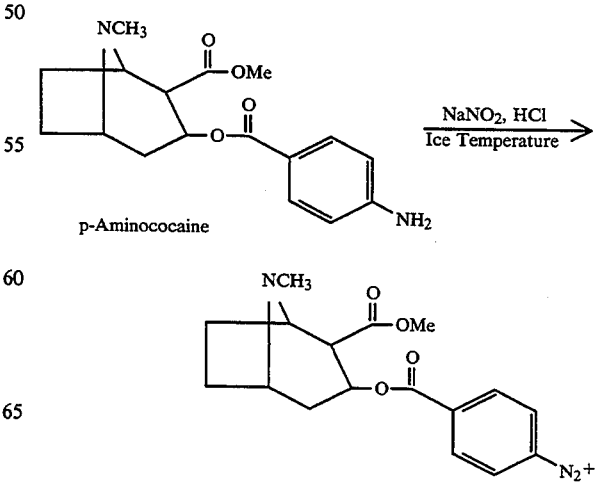

-continued

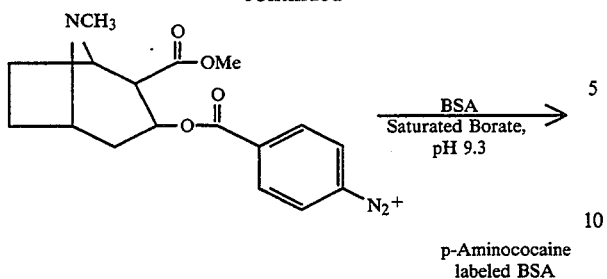

p-Aminococaine labeled BSA

The cocaine-BSA conjugate was dialyzed three times to remove unreacted p-aminococaine and filter sterilized. Injections were made into a rabbit and after antibodies had developed the rabbit was bled. The plasma was diluted 50% with phosphate buffer and affinity purified. The affinity column was prepared from Affi-Gel 10 (an activated solid support) and p-aminococaine. The bound antibodies were removed by elution with 0.01M HCl, dialyzed against 0.1M ammonium carbonate and freeze dried.

The preparation of the cocaine-enzyme conjugate is outlined below:

The preparation of the cocaine-enzyme conjugate is outlined below:

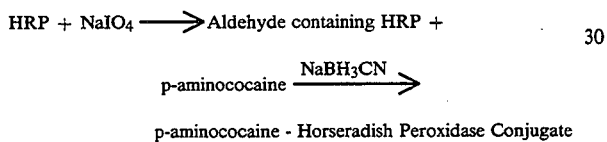

p-aminococaine - Horseradish Peroxidase Conjugate

This conjugate was analyzed by gel isoelectric focusing on polyacrylamide gels. The detection of the enzyme was made by applying the substrate to the developed gel and observing the colored bands that formed.

Various preparations of antibodies to cocaine gave varying responses when configured to MAC. For example, some preparations gave extremely good blanks—no color was evident after several hours. Other antibody preparations gave blanks that were colored. Although the drug-containing solution was darker, the blanks became the same intensity after a few minutes. The good preparations were obtained by first eluting the antibodies from the affinity column with cocaine, then with acid (0.1M). The acid eluant was used in preparing the MAC. In this procedure, the cocaine removed the low affinity antibodies leaving only the moderate and high affinity antibodies bound to the column. The acid removed the remaining high affinity antibodies. Low affinity antibodies still bind the drug-enzyme conjugate but release it very easily and cause a high blank.

Obviously, many modifications and variations of the present invention are possible in light of the above teachings. It is therefore to be understood that within the scope of the appended claims, the invention may be practiced otherwise than as specifically described.

What is claimed is:

1. A card for assaying of a suspected substance in a liquid sample, comprising:
a first layer comprising a hydrophobic portion having formed therein at least one well for receiving the liquid sample;
a second layer defining a bottom surface of said well, comprising a supporting surface of cellulose which directly and covalently binds and supports thereon a reactive species, and a control membrane, beneath said supporting surface, for controlling the velocity of liquid flow therethrough so that, if said substance is present in said sample, said substance in said sample detectably reacts with said reactive species;
a third layer underneath said well and said control membrane, comprising a polymeric superabsorbent material impregnated with a reagent which produces a signal directly proportional to the concentration of any suspected substance in the liquid sample received in said well, said superabsorbent material having an absorptive capacity of at least about 200 mL distilled water/100 $cm^2$; said third layer also including a backing beneath said superabsorbent material for supporting said superabsorbent material, said backing and said superabsorbent layer being sufficiently transparent to said signal when wet so that said signal may be detected by reading said signal through said wet backing;
a conjugated molecule selected from the group consisting of an antibody-enzyme conjugate capable of specifically binding said substance and a conjugate of said substance and an enzyme, said conjugated molecule being within said first or second layer and said reagent comprising a substrate for said enzyme;
said reactive species being a binding partner for said conjugated molecule, said binding partner being selected from the group consisting of:
(i) an antibody capable of specifically binding said conjugate of said substance and said enzyme; and
(ii) said substance.

2. The card of claim 1, wherein said supporting surface is a membrane surface.

3. The card of claim 1, wherein said first layer of said card includes said antibody-enzyme conjugate or said substance enzyme conjugate and said second layer has bound thereto, respectively, said substance or said antibody.

4. The card of claim 1, wherein said second layer of said card includes said antibody-enzyme conjugate or said substance-enzyme conjugate and further includes, respectively, said substance or said antibody immobilized thereon.

5. The method of claim 1, wherein said control membrane is a semipermeable membrane.

6. A card for microassaying of a suspected substance in a liquid sample, comprising:
a first layer comprising a hydrophobic portion having formed therein at least one well for receiving said liquid sample;
a conjugated molecule disposed within said first layer so as to be carried into said second layer by said liquid sample received in said at least one well, said conjugated molecule being selected from the group consisting of an antibody-enzyme conjugate capable of specifically binding said substance and a conjugate of said substance and an enzyme;
a second layer defining a bottom surface of said well, comprising a supporting surface of cellulose, which supports and is directly attached by chemical bonding to a reactive species, said second layer including a control membrane, beneath said supporting surface, for controlling the velocity of liquid flow therethrough so that, if said substance is present in said sample, said substance in said sample detectably reacts with said reactive species;

a third layer underneath said well and said control membrane for controlling the velocity of liquid flow, comprising a polymeric superabsorbent material impregnated with a substrate for said enzyme, said enzyme and said substrate being selected so that the action of said enzyme upon said substrate causes a detectable change in the intensity of the absorption or emission spectrum of said third layer of a magnitude directly proportional to the concentration of any of said suspected substance in said liquid sample received in said well, said superabsorbent material having an absorptive capacity of at least about 200 mL distilled water/100 cm$^2$; said third layer also including a backing beneath said superabsorbent material for supporting said superabsorbent material, said backing and said superabsorbent material being sufficiently transparent to said change in the absorption or emission spectrum when wet so that said signal may be detected by reading said signal through said wet backing;

said reactive species being a binding partner for said conjugated molecule, said binding partner being selected from the group consisting of:
(1) an antibody capable of specifically binding said conjugate of said substance and said enzyme; and
(2) said substance.

7. The card of claim 6, wherein said supporting surface is a membrane surface.

8. The card of claim 6, wherein said antibody is a monoclonal antibody.

9. The card of claim 6, wherein said substance is directly bound to said supporting surface and said first layer includes said antibody-enzyme conjugate.

10. The card of claim 6, wherein said substrate for said enzyme is a reduced dye precursor.

11. The card of claim 10, wherein said enzyme is horseradish peroxidase.

12. The card of claim 11, wherein said superabsorbent layer further comprises a source of hydrogen peroxide.

13. The card of claim 12, wherein said source of hydrogen peroxide is sodium peroxide or sodium perborate.

14. The card of claim 10, wherein said reduced dye is a combination of 4-chloro-1-naphthol and N,N-diethylphenylenediamine; N,N-dimethylphenylenediamine; or a combination of 3-methyl-2-benzothiazolinone hydrazone hydrochloride and dimethylaminobenzene carboxylic acid.

15. The card of claim 6, wherein said first layer of said card further comprises at least one positive control well for receiving said liquid sample and providing said detectable change even in the absence of said substance in said liquid sample, and at least one negative control well for receiving said liquid sample, and not exhibiting said detectable change even in the presence of said substance in said sample.

16. The card of claim 6, wherein said enzyme is alkaline phosphatase.

17. The card of claim 6, wherein said indicator is bromocresolsulfophthalein monophosphate.

18. The method of claim 6, wherein said control membrane is a semipermeable membrane.

* * * * *